(12) United States Patent
Zalunardo

(10) Patent No.: US 10,656,122 B2
(45) Date of Patent: May 19, 2020

(54) ASSEMBLY FOR DETECTING GAS CONTAINED IN A LIQUID

(71) Applicant: INFOMED SA, Acacias (CH)

(72) Inventor: Ivano Zalunardo, Châtelaine (CH)

(73) Assignee: INFOMED SA, Acacias (CH)

( * ) Notice: Subject to any disclaimer, the term of this patent is extended or adjusted under 35 U.S.C. 154(b) by 156 days.

(21) Appl. No.: 15/915,804

(22) Filed: Mar. 8, 2018

(65) Prior Publication Data

US 2018/0266994 A1 Sep. 20, 2018

(30) Foreign Application Priority Data

Mar. 14, 2017 (EP) .................................... 17160721

(51) Int. Cl.
*G01N 29/02* (2006.01)
*A61M 1/36* (2006.01)
(Continued)

(52) U.S. Cl.
CPC ............ *G01N 29/02* (2013.01); *A61M 1/3626* (2013.01); *A61M 5/365* (2013.01); *G01N 21/59* (2013.01); *G01N 29/032* (2013.01); *G01N 29/221* (2013.01); *G01N 29/222* (2013.01); *G01N 29/223* (2013.01); *G01N 29/2462* (2013.01); *A61M 2205/12* (2013.01); *A61M 2205/3306* (2013.01); *A61M 2205/3375* (2013.01); *G01N 21/51* (2013.01); *G01N 2201/08* (2013.01); *G01N 2291/021* (2013.01); *G01N 2291/022* (2013.01); *G01N 2291/02433* (2013.01); *G01N 2291/044* (2013.01); *G01N 2291/048* (2013.01); *G01N 2291/101* (2013.01); *G01N 2291/102* (2013.01)

(58) Field of Classification Search
CPC ........... G01N 2021/0112; G01N 21/59; G01N 2021/8405; G01N 2201/08; G01N 29/02; G01N 29/024; G01N 29/22; G01N 29/221; G01N 29/222; G01N 29/2462; A61M 1/3626; A61M 2205/3306; A61M 2205/3375
USPC ....... 73/19.01, 19.03, 19.1, 61.48, 627, 632, 73/642, 861.27
See application file for complete search history.

(56) References Cited

U.S. PATENT DOCUMENTS 3,921,622 A 11/1975 Cole
5,179,862 A 1/1993 Lynnworth
(Continued)

FOREIGN PATENT DOCUMENTS

EP 2 006 543 A1 12/2008
WO 2015/191775 A1 12/2015

OTHER PUBLICATIONS

European Search Report issued in Application No. 17160721, dated Jul. 10, 2017.

*Primary Examiner* — Benjamin R Schmitt
(74) *Attorney, Agent, or Firm* — Young & Thompson

(57) ABSTRACT

Disclosed is an assembly for detecting the presence of a gas in a liquid contained or circulating in a conduit including an element for supporting the conduit and a sensor allowing the transmission and reception of acoustic or light waves. The sensor is arranged on the support of the conduit facing the one and the same side of the conduit and the support element includes a waveguide capable of routing the wave transmitted by the transmitter of the sensor to the receiver of the sensor.

12 Claims, 2 Drawing Sheets

(51) Int. Cl.
    *G01N 29/22*     (2006.01)
    *G01N 29/032*     (2006.01)
    *G01N 29/24*     (2006.01)
    *A61M 5/36*     (2006.01)
    *G01N 21/59*     (2006.01)
    *G01N 21/51*     (2006.01)

(56) References Cited

U.S. PATENT DOCUMENTS

| | | | |
|---|---|---|---|
| 5,583,280 A | 12/1996 | Mo et al. | |
| 6,895,823 B1 * | 5/2005 | Herrmann | G01F 1/662 73/861.23 |
| 8,033,157 B2 | 10/2011 | Yardimci et al. | |
| 8,313,314 B2 | 11/2012 | Favre | |
| 8,986,252 B2 | 3/2015 | Cummings et al. | |
| 2017/0122916 A1 | 5/2017 | Leaders et al. | |

\* cited by examiner

ASSEMBLY FOR DETECTING GAS CONTAINED IN A LIQUID

FIELD OF THE INVENTION

Background of the Invention

The present invention relates to a device that allows the presence of gas in a liquid contained or circulating in a conduit to be detected.

Description of the Related Art

Many situations require the presence of gas, often air, to be identified in a liquid contained or circulating in a conduit. In the medical field, for example, it frequently involves detecting the presence of air, the injection of which can prove to be harmful to the patient, in a conduit containing a liquid that is injected into a patient, for example, blood or a medicinal product.

The same is the case in the fluid circulation systems that are used in the field of extracorporeal purification of patients suffering from kidney failure, for example, and treated using known methods, such as dialysis or haemofiltration. However, the invention is not limited to this particular field.

In order to differentiate a pure liquid from a liquid containing a gas, such as air, for example, means have already been described that particularly use ultrasonic transmitters and receivers. Such a system is disclosed, for example, in U.S. Pat. No. 3,921,622, which comprises an ultrasonic transmitter and receiver placed on either side of the conduit in which the fluid to be analysed circulates. This conduit is formed by a tube that is slightly compressed between the two parts comprising the transmitter, on the one hand, and the receiver, on the other hand. The disclosed system comprises electronics that supply the transmitter, which generates an ultrasonic wave that propagates through the conduit to the receiver, which then generates an electric current corresponding to the received signal. The signal is then processed by the electronics in order to detect the possible presence of gas in the liquid circulating between the components (transmitter and receiver) of the sensor.

U.S. Pat. No. 5,583,280 improves the technique of assembling the sensor, particularly by replacing the two movable parts comprising the transmitter and the receiver with a moulded U-shaped part, at the centre of which the conduit will be placed, the transmitter and the receiver for their part being adhered on either side of the arms forming the U-shape using a method that further enhances the simplification of the assembly.

In addition to the requirement for detecting the possible presence of gas in a conduit, there is often a requirement for the ease of operation of a complex system, as well as production cost constraints, particularly for single-use equipment, which by definition is mass-produced. A known solution to this problem is to integrate as many elements as possible into a cassette. These elements are, for example, cavities for membrane pumps, zones for clamping or for measuring pressures, the colour of the flowing fluid or the presence of air in an injected fluid such as, for example, the patient's blood, which is re-administered to them after it is purified. An example of such a cassette is disclosed in U.S. Pat. No. 8,033,157, which includes a narrowed fluid circulation zone, around which a transmitter is placed opposite a receiver, with the assembly forming a sensor for detecting any air bubbles in the liquid.

In general, these cassettes are fairly complex to manufacture, they have a plurality of elements, often moulded parts, which must be precisely adjusted relative to each other, and as many manufacturing and assembly steps, each time with associated costs and risks, for example, a disjoined assembly or burrs resulting from the injection of material.

One possibility for simplifying the production of such cassettes is to design a cassette that is produced with only one moulded part, which is usually rigid and comprises cavities, and a flat part, which is obtained, for example, by extrusion and which is usually flexible and is called "membrane" hereafter, and which is fixed to the former by any means (solvent, ultrasonic or laser soldering, etc.). In order to benefit from the advantages of such an assembly, the moulded part should have a flat surface in order to fix the membrane and thus close the conduits created by the cavities of the moulded part in a completely sealed manner. Such a cassette and its operation has been partly disclosed in patent EP 2006543B1 in the name of the applicant. A non-flat surface for fixing the membrane is possible but increases the problems and quite often means that said membrane also has to be moulded; therefore, such a solution is not economical.

For its use, a cassette as previously described is positioned on an apparatus that comprises actuators and sensors. As is the case for the production of the cassette, the simplest and most economical solution is to arrange all the parts of the apparatus that have to interact with the cassette on one side, thus limiting the relative three-dimensional positioning and the need to have a plurality of systems for positioning the components of the apparatus on the cassette. Thus, the cassette will preferably be placed on an apparatus that comprises all the actuators and sensors on the side of the membrane that is flexible and allows non-invasive interaction with the cavities of the injected part, which prevents contamination of the fluid present in the conduits.

If pumps, clamps or sensors for pressure through a flat membrane have already been produced from the same side of the cassette, in the previously described prior art the possibility of detecting any gas bubbles in the liquid circulating in one or more conduit(s) of such a cassette is only carried out by placing a transmitter on one side of the cassette and a receiver on an opposite face. The ultrasonic signal thus passes directly through the conduit to be analysed. Such systems do not allow all the actuators and sensors to be placed on the same side of the cassette, which adds complications and costs since at least part of a sensor is located on the opposite part of the cassette, which part is also often movable in order to allow the cassette to be installed. The cables of the sensors therefore need to pass through movable elements, which increases the risk of breakages and prevents the assembly and the inspection of said sensor outside of the assembled apparatus.

Electronic assemblies connected to the ultrasonic sensors are extensively described in the prior art and can be applied in one way or another to the present invention.

Thus, in the prior art, in order to detect a gas in a liquid contained or circulating in a conduit, the transmitter is always placed opposite the receiver. Furthermore, a configuration with the transmitter and the receiver on the same side is not applicable to a cassette produced from an injected part, onto which a flexible membrane is fixed, since this does not allow the incident wave energy to be transmitted. Thus, in the previous examples it is to be noted that the ultrasonic sensors are always supported on parts made of rigid materials. This problem is less pronounced with an optical sensor, which, however, does not allow the presence of bubbles in a densely-coloured liquid such as blood to be easily distinguished and thus cannot be applied to systems such as dialysis.

SUMMARY OF THE INVENTION

An aim of the invention therefore is to provide a sensor-conduit assembly for detecting gas in a liquid contained or circulating in a conduit that is arranged in order to minimise the spatial requirement of the device, particularly in the case of a liquid contained or circulating in a cavity forming a conduit in a filtration cassette closed by a flexible membrane. Of course, other arrangements of the invention are possible, particularly that shown in FIG. 1.

Another aim of the invention is to provide such an assembly that is arranged on the same side as the other actuators and sensors when it is integrated, for example, into a more complex system, such as a dialysis cassette. Finally, a further aim of this detection assembly is for it to be able to be assembled and tested outside of the apparatus in which it will be integrated.

This aim is achieved with a detection device that is characterised by the features disclosed in claim 1.

BRIEF DESCRIPTION OF THE DRAWINGS

Further advantages are apparent from the features disclosed in the dependent claims and from the following detailed description and figures, in which:

DESCRIPTION OF THE PREFERRED EMBODIMENTS

Hereafter, "moulded part" is understood to be a component preferably produced by injecting plastic material. The shapes that allow the invention to be carried out also can be produced by machining, stamping or by any other known method for shaping plastic or metal material.

"Conduit" is understood to be any closed shape, in which a liquid can be contained or can circulate.

"Sensor" is understood to be an element that allows a wave to be transmitted and received and that generally comprises a transmitter and a receiver, the two elements actually being able to be a single element used once in transmission mode and once in reception mode. The sensor can also accommodate a plurality of transmitters and/or a plurality of receivers.

"Transmitter" is understood to be a component, which, when it is activated, for example, by an electric current, generates a wave that passes through the conduit to the receiver. Preferably, the wave is ultrasonic or optical and is generated, for example, by piezoelectric wafers or light-emitting diodes. The "receiver" is an element that is sensitive to the wave type transmitted by the transmitter, which generates a signal, for example, an electric current or voltage, corresponding to the signal that it receives. The receiver is, for example, a piezoelectric wafer or a phototransistor. When the transmitter and the receiver are actually the same component, said component is called "transceiver".

Figure 1:
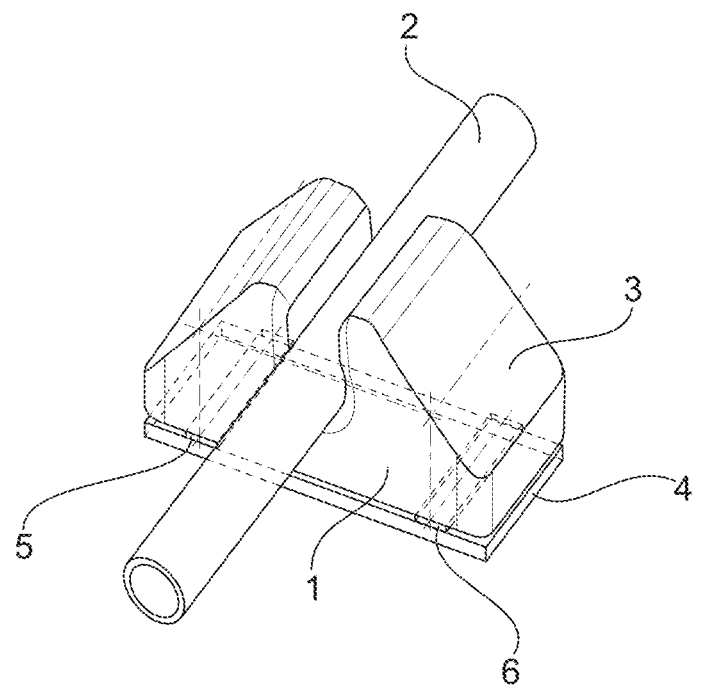
FIG. 1 schematically shows, by way of an example, a first embodiment of the detection device of the invention.

FIG. 1 schematically shows a conduit 2 formed by a flexible or rigid tube, in which a liquid can circulate or be contained. This conduit is arranged in a support 1, which has a recess at its centre that is able to accommodate the conduit 2. Typically, the conduit 2 is a limited-use tube made of plastic material that is regularly replaced, whereas the support 1 is an element that is permanently fixed to an apparatus. The support 1 has two walls at its centre that surround the conduit on each side and has, on its external sides, inclined faces 3, preferably at 45°, that form a waveguide to allow the reflection, transmission or refraction of a wave generated by a sensor 4 comprising a transmitter and a receiver that will be described in further detail hereafter. The sensor 4 is arranged on the support 1, below the conduit 2. Thus, it is to be noted that the sensor 4 is located on the one and the same side of the conduit to be analysed, contrary to the embodiments of the prior art, in which the transmitter and the receiver forming the sensor are arranged on either side of the conduit to be analysed.

Figure 2:
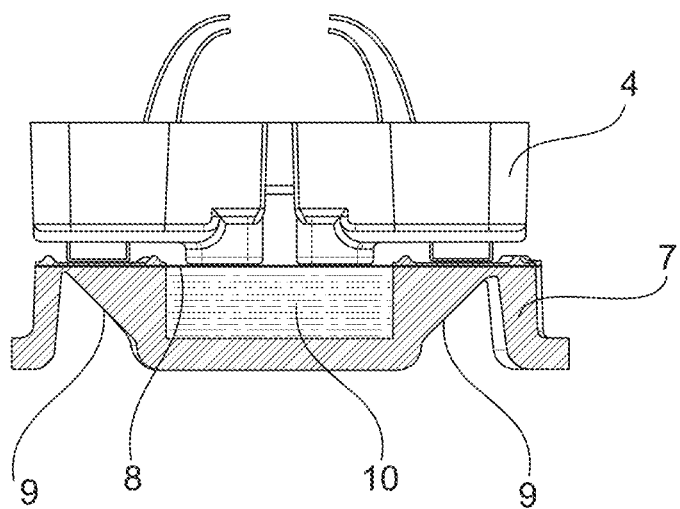
FIG. 2 schematically shows a second embodiment of the invention when the conduit is formed by a cavity of a fluid circulation cassette that is closed by a flexible membrane.

FIG. 2 shows a section view of an assembly for detecting the presence of a gas in a liquid according to the invention, which assembly comprises an electronic sensor 4 made up of a wave transmitter and a wave receiver arranged side by side in the same plane. The element for supporting the conduit is, in this preferred embodiment, formed by the body 7 of a fluid circulation cassette, such as a dialysis cassette that integrates cavities designed to create, through its membrane, pumps, clamps, pressure, blood or air sensors. Said cassette is preferably made of a rigid moulded part and a flexible extruded part.

The cassette has a recess 10, in which the liquid can circulate or be contained. A membrane 8 is fixed by any means to the rigid part 7 forming the body of the cassette. The membrane is fixed in a sealed manner and allows the cavity 10 to be sealed in order to thus form the conduit in which the liquid circulates or is contained. It is to be noted that the membrane 8 is compressed between the sensor 4 and a rigid part of the cassette, which creates the coupling required to ensure that the incident wave is transmitted to the wave guide 9.

This membrane 8 is a relatively thin plate preferably made of a flexible plastic by extrusion. Other embodiments are possible, for example, using metal sheets obtained by rolling.

The body of the cassette forming the conduit support further comprises waveguides 9 designed to allow a wave to be conveyed between the transmitter 5 and the receiver 6 of the sensor 4, which in this embodiment is preferably placed on the same side as the flexible membrane 8.

"Waveguides" 3, 9 are understood to be surfaces designed to transmit, reflect or refract the waves transmitted by the transmitter 5 to the receiver 6 after having passed through the liquid. These surfaces are, in a preferred embodiment, produced in the body of the cassette 7 as surfaces arranged at 45°. Thus, as shown in FIG. 2, the wave is transmitted by the transmitter 5 located on the left-hand side of the cassette perpendicular to the membrane 8 and is reflected horizontally towards the opposite inclined face 9, on the right-hand side of the figure, through the liquid. When the wave reaches the inclined face 9 located on the right-hand side of the cassette, it is vertically reflected towards the detector 6. Other paths for the wave are also possible, for example, by providing multiple reflections.

In order to define the path of the wave, Snell-Descartes laws are used, which allow the angle of the incident ray to be associated with those of the reflected and refracted rays and allows the reflection and transmission coefficients to be determined at the junction between two media, for example, plastic and air. By knowing the angle of incidence and the impedance of the materials that are present, which is provided in tables that are available for the main materials used in mechanics, it is thus possible to determine the intensity of the reflected ray, as well as the intensity and the angle of the refracted ray, which allows the desired geometries to be defined as a function of the various applications of the invention.

Figure 3:
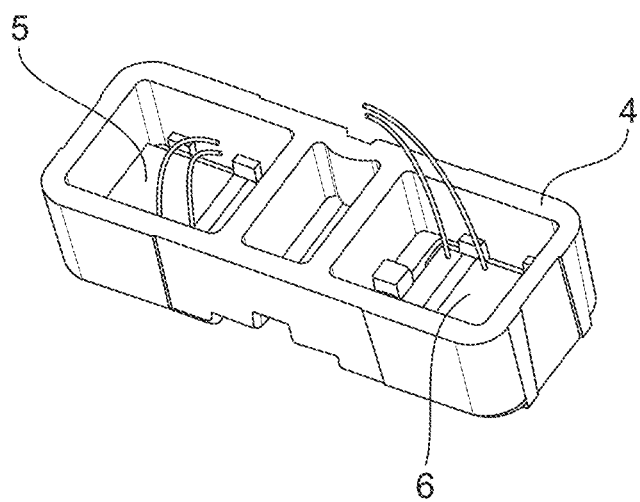
FIG. 3 is a schematic representation of a sensor comprising a transmitter and a receiver.

As is schematically shown in FIG. 3, the sensor is formed by a support 4 accommodating a transmitter 5 and a receiver 6 side by side, the transmitter 5 and the receiver 6 being able to be the same part and then being called transceiver.

In one variant, the sensor can also accommodate a plurality of transmitters and/or a plurality of receivers according to the contemplated configurations.

Preferably, the sensor is an element that can be tested independently of the apparatus intended to accommodate said sensor.

An example of a particularly advantageous application is a home dialysis device according to the invention that is applicable to patients suffering from chronic kidney failure. Dialysis involves using pumps to circulate the patient's blood in a dialyser provided with a semi-permeable membrane. On the other side of the membrane a liquid, called "dialysate", is circulated that will attract the impurities contained in the blood due to the difference in concentration present on either side of the membrane, according to a known process called "diffusion". This treatment requires an apparatus that manages the flows of blood and of dialysate, as well as the safety of the patient, a dialyser, bags containing fresh dialysate and other bags that collect the dialysate discharged from the dialyser. This treatment generally takes from 2 to 4 hours every day or every 2 days depending on the patient's condition. In certain cases, it takes place at night, for approximately 8 hours while the patient is asleep. For such a device, it is known for the blood circulation loop to be necessarily equipped with a detector for detecting the presence of air in the blood before it is re-administered to the patient.

In this particular embodiment, the dialysis device incorporating a device according to the invention advantageously comprises at least one detector formed by a cassette and a sensor as previously described.

The invention claimed is:

1. An assembly for detecting the presence of a gas in a liquid contained or circulating in a conduit, the assembly comprising:
a support element that supports the conduit, and
a sensor comprising a transmitter and a receiver, the sensor transmitting and receiving an acoustic or light wave,
wherein:
the sensor is arranged on the support element of the conduit facing a same side of the conduit,
the support element comprises a waveguide that routes the wave transmitted by the transmitter of the sensor to the receiver of the sensor,
the support element is formed by a cassette, and
the liquid conduit is formed by a recess in a body of the cassette that is sealed by a flexible membrane.

2. The assembly as claimed in claim 1, wherein the membrane is fixed between the sensor and a rigid part of the support element.

3. The assembly as claimed in claim 2, wherein the waveguide is formed by faces arranged in a body of the support element.

4. The assembly as claimed in claim 2, wherein said support element for supporting the conduit is produced in a part moulded, injected or machined in a block of material.

5. The assembly as claimed in claim 2, wherein the sensor is formed by a transmitter and a receiver placed side by side.

6. The assembly as claimed in claim 1, wherein the waveguide is formed by faces arranged in a body of the support element.

7. The assembly as claimed in claim 6, wherein the faces forming the waveguide form a 45° angle with the vertical plane.

8. The assembly as claimed in claim 7, wherein said support element for supporting the conduit is produced in a part moulded, injected or machined in a block of material.

9. The assembly as claimed in claim 6, wherein said support element for supporting the conduit is produced in a part moulded, injected or machined in a block of material.

10. The assembly as claimed in claim 1, wherein said support element for supporting the conduit is produced in a part moulded, injected or machined in a block of material.

11. The assembly as claimed in claim 1, wherein the sensor is formed by a transmitter and a receiver placed side by side.

12. The assembly as claimed in claim 1, wherein the sensor is formed by a transceiver.

* * * * *